US008603505B2

(12) United States Patent
Brown et al.

(10) Patent No.: US 8,603,505 B2
(45) Date of Patent: *Dec. 10, 2013

(54) COSMETIC COMPOSITION CONTAINING NOVEL FRACTAL PARTICLE BASED GELS HAVING IMPROVED OPTICAL PROPERTIES

(75) Inventors: Steven E. Brown, New Windsor, NY (US); Ernest S. Curtis, Milford, PA (US)

(73) Assignee: Avon Products, Inc., New York, NY (US)

( * ) Notice: Subject to any disclaimer, the term of this patent is extended or adjusted under 35 U.S.C. 154(b) by 772 days.

This patent is subject to a terminal disclaimer.

(21) Appl. No.: 11/643,573

(22) Filed: Dec. 21, 2006

(65) Prior Publication Data

US 2008/0152680 A1    Jun. 26, 2008

(51) Int. Cl.
*A61Q 19/08* (2006.01)
*A61Q 1/00* (2006.01)
*A61K 8/06* (2006.01)

(52) U.S. Cl.
USPC ............... 424/401; 424/9.411; 424/78.09

(58) Field of Classification Search
USPC .................. 424/9.411, 78.09, 401
See application file for complete search history.

(56) References Cited

U.S. PATENT DOCUMENTS

| | | | |
|---|---|---|---|
| 5,509,960 A * | 4/1996 | Simpson et al. ............. 106/437 |
| 6,309,627 B1 | 10/2001 | Gotz-Berner et al. | |
| 6,703,027 B2 | 3/2004 | Kurosawa et al. | |
| 6,740,590 B1 * | 5/2004 | Yano et al. .................... 438/692 |
| 6,896,889 B2 | 5/2005 | Chevalier et al. | |
| 2003/0072780 A1 | 4/2003 | Ionita-Manzatu et al. | |
| 2004/0137026 A1 * | 7/2004 | Golz-Berner et al. ........ 424/401 |
| 2005/0163813 A1 * | 7/2005 | Kosbach et al. .............. 424/401 |
| 2005/0201961 A1 * | 9/2005 | Lu et al. ......................... 424/63 |
| 2006/0067906 A1 * | 3/2006 | Sanders ..................... 424/70.12 |
| 2006/0078527 A1 * | 4/2006 | Midha et al. ............... 424/70.27 |
| 2006/0127332 A1 * | 6/2006 | Rodrigues et al. ............. 424/63 |

FOREIGN PATENT DOCUMENTS

| CA | 2294933 A1 | 2/1999 |
| EP | 123097 A1 | 8/2002 |
| JP | 2005-336161 | 12/2005 |

OTHER PUBLICATIONS

"In-vitro Method of Quantification of Soft Focus Effect of Particulates," Pascal Delrieu, NYSCC Scientific Meeting, New York City, Dec. 8-9, 2005.

* cited by examiner

*Primary Examiner* — Brian-Yong S Kwon
*Assistant Examiner* — Courtney Brown
(74) *Attorney, Agent, or Firm* — David M. Joyal; Joan M. McGillywddy; Brian C. Remy

(57) ABSTRACT

A method of instantly reducing the appearance of wrinkles and skin imperfections while smoothing the skin, which comprises applying a cosmetic composition in the form of an oil-in-water emulsion comprising a fractal particle based gel and refractive index matching polymers with respect to at least one of the fractal particles. The composition of the invention provides both optical blurring and skin smoothing effect on the skin.

36 Claims, 5 Drawing Sheets

COSMETIC COMPOSITION CONTAINING NOVEL FRACTAL PARTICLE BASED GELS HAVING IMPROVED OPTICAL PROPERTIES

FIELD OF THE INVENTION

The present invention relates to cosmetic compositions and more particularly, to cosmetic compositions with both optical blurring and space filling effects for improved surface appearance of biologic substrates such as skin and lips.

BACKGROUND OF THE INVENTION

A number of methods have been developed to reduce wrinkles and minimize fine lines. Some of these methods include active ingredients such as antioxidants; agents that act by neurotransmission inhibition in nerve cells such as botulinum toxin (Botox™) (Allergan, Irvine, Calif.), thereby relaxing contracted muscles; agents that accelerate the cell renewal process such as hydroxy and fruit acids like retinoic acid; emollients such as shea butter; skin plumpers such as hyaluronic acid; fillers such as collagen; light-diffusing pigments and microspheres which create the illusion that wrinkles have disappeared. Other methods have been developed to reduce the appearance of pores, skin surface unevenness and imperfections and the like. Some of these methods include skin lightening agents, and filling and camouflaging the skin.

Unfortunately, many cosmetic foundations and make-ups actually accentuate wrinkles and fine lines due to migration of the pigments into the wrinkle crevices. Other products cover the skin imperfections but create an unnatural, caked-on appearance. Others, such as mica, reflect rather than diffuse and scatter light, thereby resulting in a shiny appearance. Additionally, some of these methods are not immediate, requiring days and weeks of continued use to see effects. Others are invasive, requiring injections, patient discomfort, and may entail redness, swelling and other side effects.

Foundations in the form of oil-in-water emulsions are well known. However, these compositions merely cover the skin and often impart a white cast to the skin. Attempts have been made to provide foundations which result in either optical blurring or space filling, but not both.

Therefore, the need exists for alternative methods to provide a natural and smooth appearance to the skin with visible reduction in wrinkles, fine lines, pores, and skin imperfections but which overcome the problems associated with previous methods and compositions and would represent a significant advance in cosmetic art.

The present invention fulfills such a need. The inventors have discovered that fractal particle gels containing a refractive index matching polymer (as herein described) can be incorporated into a cosmetic formulation, which, when applied to a biologic substrate such as skin or lips, creates a film that is both optically blurring to diffuse the transmission of light from the surface of the film, and space filling to effect smooth skin surfaces and thus conceal fine lines and wrinkles. None of the existing art provides the advantages and benefits of the present invention.

SUMMARY OF THE INVENTION

It is an object of the present invention to provide cosmetic compositions comprising "optical gels" having a fractal gel network of oppositely charged nanoparticles, and a polymer whose refractive index matches the refractive index of one of the fractal particles, to achieve space filling for smoothing application surfaces, and optical blurring to diminish and potentially substantially eliminate any chalky appearance of the composition or of a second cosmetic composition applied as a topcoat.

It is an object of the present invention to provide a method to optimize the optical diffusion of light, i.e. optical blurring, and consequently cause the appearance of wrinkles, fine lines, pore and skin imperfections to vanish while allowing the skin to appear natural, smooth and flawless.

It is a further object of the present invention to provide a cosmetic composition having unique optical blurring properties and the ability to smooth fine lines and wrinkles without imparting a white cast to the skin.

It is yet another object of the present invention to provide a cosmetic composition containing a gel network comprised of two or more types of submicron sized fractal particles having opposite surface charges (zeta potential) at a given pH and a refractive index matching polymer (as hereinafter described).

It is yet another object of the present invention to provide a cosmetic composition comprising a cosmetically suitable medium, such as aqueous, nonaqueous, water-in-oil, and oil-in-water emulsions, containing a fractal gel and a refractive index matching polymer.

A further object of the present invention is to provide a fractal gel and a refractive index matching polymer wherein the refractive index matched particles become "invisible", yet are physically dispersed on the nano scale.

It is a further object of the present invention to provide a cosmetic composition having unique space filling properties to topographically smooth lines and wrinkles of the skin surface, while providing optically desirable light diffusing properties.

It is yet another object of the present invention to provide a cosmetic composition comprising a fractal gel primer composition to provide a smooth surface and blurring effect for use with a topcoat cosmetic composition, wherein the application and look of the topcoat composition applied on top of the primer composition is enhanced due to the light diffusing effect of the primer composition layer.

Further according to this and other objects and advantages of the present invention are provided methods for blurring wrinkles, fine lines, pores, skin surface unevenness and imperfections while providing a surface smoothing effect by space filling via a gel network. The method includes layering an optical blurring/smoothing layer onto the skin in conjunction with a topcoat pigmented layer to make the skin appear to be light releasing and brighter.

In another aspect of the invention, the present invention is applicable to human skin in any cosmetically acceptable vehicle.

In another aspect of the invention the compositions are suitable as hair treatment products, especially as mascaras to treat thinning hair, in light of the porous, reticulated structure, which provides a volumizing benefit the hair shaft.

These novel features of the present invention will become apparent to those skilled in the art from the following detailed description, which is simply, by way of illustration, various modes contemplated for carrying out the invention. As will be realized, the invention is capable of additional, different obvious aspects, all without departing from the invention. Accordingly, the Figures and specification are illustrative in nature and not restrictive.

DETAILED DESCRIPTION OF THE INVENTION

Figure 1:
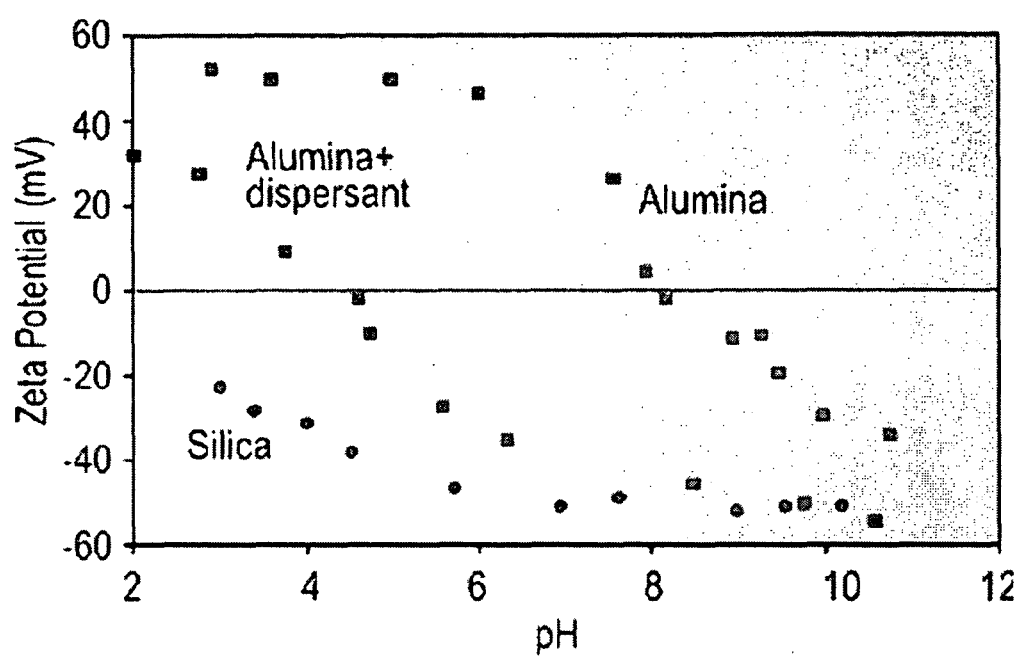
FIG. 1 is a graphical plot of the zeta potential of various metal oxides as a function of pH.

The cosmetic composition of the present invention comprises (i) a fractal particle based gel ("fractal gel" or "optical gel") comprising a first fractal particle and a second fractal particle, the first and second fractal particles having opposite net surface charges (zeta potential), and (ii) at least one polymer having a refractive index that matches the refractive index of at least one of the first or second fractal particles.

The fractal particle gel network has an open, reticulated structure, with size domains and refractive indices for the fractal particles adapted to effectively fill wrinkles and other surface imperfections in the skin, thus providing a surface smoothing effect to the skin. Accordingly, when applied to skin, the cosmetic composition provides a natural, smooth and youthful appearance with visible reduction in wrinkles and skin imperfections. The open structure of the fractal gel matrix thus fills the wrinkles with a film of significantly lower packing density that minimizes and even avoids the undesirable chalky appearance of conventional cosmetic products. Moreover, the open structure of the gel matix provides significant surface area for sebum absorption, thus improving wear for the cosmetic composition, and without the extensive use of film formers.

Another beneficial aspect of the invention is the ability of the fractal particle gel network to display unique rheological properties, which are especially useful in cosmetic applications. The gel network is highly thixotropic. That is to say, the viscosity of the gel rapidly diminishes under increasing shear stress, yet the gel network reforms quickly once the shear stress is removed. Effectively, this imparts an effect wherein the composition transforms from viscous, non-flowing compositions to a free flowing liquid when the composition is applied, e.g., with a brush or other applicator. The speed at which the network reforms to a gel is a function of particle concentration and the magnitude of the attractive interaction between the oppositely charged particles (refer to section "Surface Charge of Particulate Dispersions"). Hyper thixotropic compositions are particularly useful in foundations, mascaras, hair care, lip compositions, and personal care compositions where low viscosity is desired during application, yet a rapid increase in viscosity is important to prevent migration of the applied composition.

When formulated to include a polymer whose refractive index matches the refractive index of one of the primary particles, the cosmetic compositions of the present invention also exhibit an optical blurring effect. That is, light incident on a film of the cosmetic compositions of the present invention that has been provided on skin exhibits diffused transmittance and diffused reflectance, both properties altering the way light scatters and/or reflects from the skin's surface and resulting in a soft light effect. The soft light effect coupled with the surface filling of wrinkles and other imperfections imparts a younger, fresher visual appearance to the surface of the skin characterized by a dramatic reduction in the appearance of wrinkles and fine lines.

The term "optical blurring" as used herein refers to optical reduction of wrinkles, fine lines, skin surface unevenness and imperfections.

The term "fractal particles" as used herein refers to geometric particles of varying fractal dimension or in-built reticulated structure; that is, having Hausdorff-Besicovitch dimensions greater than their topological dimensions.

The expression "cosmetically acceptable vehicle" refers to a medium that is compatible with keratin materials such as human skin.

The term "particles" or particles" as used herein encompasses all particles present in the compositions of the present invention, including fractal particles, pigment particles, binders, filler, and the like, that are insoluble in the composition.

Except where specific examples of actual measured values are presented, numerical values referred to herein should be considered to be qualified by the word "about."

The terms "a" and "an", as used herein and in the appended claims, mean "one or more" unless otherwise indicated herein.

All percentages and ratios referred to herein are by weight of total composition (i.e., the sum of all components present), unless otherwise indicated.

Fractal Particles

The first essential component is a gel network having first and second submicron sized fractal particles having opposite surface charges at a given pH. Referring to FIG. 1, at pH below 7-8, the metal oxides silica and alumina have opposite surface charge or zeta potential. The first or second fractal particles that form the fractal gel most typically have different refractive indices.

The first or second fractal particles that form the fractal gel may each comprise two or more different fractal particles having the same charge. The two or more different first (or second) fractal particles of the same charge may have different sizes, different net surface charges (of the same type, however), or different refractive indices. However, it is preferred that all fractal particles to which the refractive index of the polymer is matched have substantially the same refractive index. It is most preferred that the fractal particle whose refractive indexed is matched by the polymer be a single type of fractal particle, i.e., all silica or all alumina.

A brief description of fractal particle geometry follows:

Fractal objects are characterized by a recursive self-similarity. In general, the fractal nature can be described mathematically by a power law relationship taking the form:

$$Y = c * X^d \tag{1}$$

where c is a constant. Therefore, if data adhere to a power law relationship, a plot of log (Y) versus log (X) will yield a straight line with slope d.

Analogously, self-similar fractals, a class of Hausdorff-Besicovitch dimensionality, rely on the object being self-similar at different length scales. The power law is consistent with this case following:

$$A=(1/s)^D \quad (2)$$

where A is the number of identical parts, s is the reduction factor and D is the self-similar dimension measure of the fractal. Equation 2 can be arranged as the following $$D=\log(A)/\log(1/s) \quad (3)$$

For example, the sides of a unit square are divided in half, forming 4 pieces, therefore A=4, s=½ thus D equals 2. Likewise a Sierpinski Gasket, wherein the original triangle side is halved, three triangle pieces are formed. Thus, A=3, s=½ and D=1.5850. Comparatively, consider a unit line segment. Dividing the line in half results in 2 equal parts, and so on. Therefore, A=2, s=½ D=1. It is important to note, the value of D agrees with the topological dimension of the line, yet a line is not fractal. Accordingly, fractals are those objects wherein the Hausdorff-Besicovitch dimension exceeds its topological dimension.

Furthermore, fractals can be classified according to their self-similarity. There are three basic types of self-similarity expressed in fractals. Exact self-similarity (the strongest type of self-similarity). The fractal appears identical at different length scales. Fractals of this type are described by displaying exact self-similarity.

Quasi-self-similarity (non-exact form of self-similarity). The fractal appears approximately identical at different length scales. Quasi-self-similar fractals are comprised of distorted and degenerate copies.

Statistical self-similarity (weakest type of self-similarity). The fractal is described by statistical measures, which are preserved across the length scale. Random fractals are examples of fractals, which are statistically self-similar, but not exact or quasi self-similar. The nature of similarity of fractals can also be described by mathematical functions.

Most fractal objects of interest do not have a readily apparent self-similar nature. Therefore, a convenient method to determine the fractal dimension of the object is the box counting method. This method is widely used and a direct method to measure the fractal dimension objects via image analysis. An object image is projected on a grid of known dimensions. Subsequently, the number of blocks that the image touches is counted. This data yields the number of blocks (N) and the block size (reduction factor, s). The grid is resized, and the process is repeated. A plot of the data, where the x-axis is log (s) and the y-axis is log (N(s)) using equation 3, yields a slope of value D.

Image analysis is particularly useful to evaluate the fractal dimension of particulates. Specifically, transmission electron spectroscopy (TEM) is well adapted to evaluate the fractal dimension of complex particulate structures. Of particular interest are fractal particles that are comprised of non-overlapping primary particles, which form a larger aggregate structure. Typically, particles of this nature are manufactured by a fuming process or complex precipitation process.

Evaluation of the mass fractal dimension of particles formed from aggregates of smaller primary particles involves determination of the number of primary particles per aggregate. Typically, this is achieved by evaluating TEM micrographs using digital imaging processing techniques. The number of primary particles per aggregate (N) is determined by dividing the projected area of the aggregate (Aa) by the projected area of the monomer unit (Am):

$$N=(Aa/Am)^\alpha \quad (4)$$

where α is an empirical fitting parameter, typically 1.0-1.1. Therefore, the Hausdorff dimension implies the relationship between the primary particle size (dp), the area radius of gyration (Rg), and the number of primary particles (N) describes the fractal dimension (Df) of the aggregate:

$$N=kf(Rg/dp)^{Df} \quad (5)$$

where kf is a constant fractal prefactor. A plot of log (N) vs. log (Rg) results in a linear plot of slope Df. Typical Df values for fractal particles of the present invention obtained by a fuming process range from 1.5-1.9, while fractal particles of the present invention obtained by a precipitation process range from 2-2.8.

Additional test methods base on rheological measurements and light scattering measurements can be used to elucidate the dimensionality of fractal particles.

The admixture of the first and second fractal particles (hereinafter also referred to as the positive fractal particles and the negative fractal particles) in a suitable vehicle causes gelation in light of charge neutralization of the oppositely charged particles. Moreover, the fractal nature of the particles results in a porous matrix structure. In another embodiment the porous matrix structure of the fractal gel may receive one or more active substances, as herein described.

The size domains and refractive indices of the fractal particles are chosen to effectively fill wrinkles and mask skin imperfections. The fractal particle network forms an open structure, which provides a surface smoothing effect. Thus, the composition can provide a natural, smooth and youthful appearance with visible reduction in wrinkles and skin imperfections.

Combining aqueous dispersions of each particle type forms a highly structured gel network as a result of charge neutralization. Typically, the fractal gel may comprise between about 5% to about 75%, preferably about 10-40%, most preferably about 20-40% solid fractal particles by weight of the fractal gel. In some instances the particles are provided by the manufacturer as a dispersion. Suitable commercially available metal oxide dispersions are Cab-o-Sperse™ PG01, PG063, PG003, PG0042, and AeroDisp™ W1836, W630 supplied by Cabot Corporation and Degussa, respectively. It is also possible to provide nonaqueous dispersions that can be used to form a nonaqueous gel phase. Such dispersion media must be able to maintain the surface charge of the fractal particle, typically requiring trace quantities of a charge control agent such as tetrabutyl ammonium benzoate, so that charge neutralization may occur. Suitable dispersion media that may be used are hydrocarbons such as isododecane, simple esters, and silicone fluids such as cyclomethicone (Ionization of metal oxide surface in non aqueous media: Labib, M. E.; Williams, R. J.; *J. Colloid Interface Sci.* 1984, 97, 356; Labib, M. E.; Williams, R. J.; *J. Colloid Interface Sci.* 1987, 115, 330; Fowkes, et al., "Mechanism of Electric Charging of Particles In Nonaqueous Dispersions", *Journal of the American Chemical Society*, vol. 15, 1982.; Fowkes, et al., "Steric And Electrostatic Contributions To The Colloidal Properties of Nonaqueous Dispersions", *Journal of the American Chemical Society*, vol. 21, 1984.; Huang, Y. C., Sanders, N. D., Fowkes, F. M., Lloyd, T. B. "The Impact of Surface Chemistry on Particle Electrostatic Charging and Viscoelasticity of Precipitated Calcium Carbonate Slurries". National Institute of Standards and Technology Special Publication 856, USA Department of Commerce, 180-200 (1993)).

Any suitable metal oxide fractal particles or derivatives thereof that achieve the desired effect may be employed. Preferably, the inorganic nanoparticles particles are fractal metal oxide particles having a diameter of between about 50-300 nm, preferably about 100-250 nm, and more preferably about 125-200 nm. Diameter as used herein refers to the diameter of a sphere that encompasses the fractal particle. Diameter may be determined by methods known in the art, e.g., light scattering and TEM. Furthermore, each nanoparticle type has a particle surface area between about 50 to 400 $m^2/g$, and more particularly between about 100 to 250 $m^2/g$. The fractal dimension of the nanoparticle is below about 2.7, preferably ranges from about 1.2 to 2.5, more preferably from about 1.5 to 2.2. Generally, as fractal dimension decreases, the concentration of solids in the gel decreases, and as surface area increases, fractal dimension also decreases.

While not common, fractal organic particles are known and can be used in accordance with the present invention, provided the requisite surface charge characteristics are met. For example, organic polyacrylates and their derivatives have fractal dimensionality and may be surface charged. Preferred organic polyacrylate particles are lauryl methacrylate/dimethyl acrylate crosspolymer (available from Amcol Health and Beauty Solutions).

The fractal particles may be selected from the group consisting of silica, alumina, titania, zirconia, zinc oxide, indium tin oxide, ceria, and mixtures thereof. Particles may be formed as part of a fuming process or a precipitation process wherein the metal oxide particle is fractal in dimension. Particles formed by the fuming process are preferred. Alumina is known to impart high diffuse transmittance, high reflectance, high scattered reflectance and low total reflectance in the visual spectra, and is a preferred first fractal particle. Silica is preferred because it has a refractive index that is substantially matchable to common cosmetic media, especially silicone oils. As shown in FIG. 1, silica is available with a net surface charge that is opposite to that of alumina at a pH value of most cosmetic formulations, that is, at a pH below about 7-8. Accordingly, silica is a preferred second fractal particle, especially when used in conjunction with alumina at a composition pH less than about 7 to 8.

Examples of suitable fractal particles include, but are not limited to, fumed silicas sold by Degussa under the tradename Aerosil, including hydrophilic and hydrophobic fumed silicas, for example, the Aerosil R-900 series, A380™ fumed silica (manufactured by Degussa), OX50™ (manufactured by Degussa), colloidal silica such as the Cabosil™ line (manufactured by Cabot), fumed alumina such as SpectrAl™ (manufactured by Cabot), and fumed titania. Preferred is fumed silica, fumed alumina, fumed titania (Degussa W740X), fumed zirconia (Degussa W2650X, W2550X), fumed ceria (Degussa Adnano), fumed zinc oxide (Degussa Adnano), fumed indium tin oxide (Degussa Adnano) or mixtures thereof.

Cosmetic compositions according to the invention may comprise from about 1-100% fractal gel by weight of the cosmetic composition. The broad range reflects the range of different types of cosmetic products and the various product forms; namely, gels, emulsions, and dispersions. Typically, the fractal gel will be at least about 5% and more typically greater than 10% fractal particles, and generally not more than about 70%, preferably 50% fractal particles. Amounts of the gel in the cosmetic compositions of the invention are also discussed later. Useful fractal gel compositions may include alumina and silica, titania and silica, zirconia and silica, and other combinations of particulates described within.

In a typical embodiment, the weight ratio of alumina to silica is 1:1 to 9:1 and is present as a dispersion in water wherein the alumina surface area is between 50 to 200 $m^2/g$ and the silica surface area is between about 300 to 400 $m^2/g$.

Suitable gels can be formed by using Spectral 51 or Spectral 80 (Cabot Corporation) fumed alumina and Cab-o-Sil M5, Cab-o-Sil EH-5. Furthermore, dispersions of metal oxides can be chosen based on their surface charge characteristics as determined by zeta potential measurements.

Charged particles are subject to electrophoresis, that is to say, in the presence of an electric field they move with respect to the liquid medium in which they are dispersed. The region between the particle and the liquid is known as the plane of shear. The electric potential at the plane of shear is called the zeta potential. The magnitude and sign of this potential can be experimentally determined using commercially available equipment. Typically, to achieve colloidal stability, (i.e. prevent flocculation), charged particulates are required to have a minimum Zeta potential of approximately 25 mV.

Selection of fractal particle pairs can be chosen based on the magnitude and sign (positive or negative) of the zeta potential at a given pH. Preferably, the magnitude and sign of the zeta potential of each particle type is sufficient, such that when combined, a non-settling, semi-rigid gel structure is formed. Preferred dispersions of the first particle type have a zeta potential values of about +10 mV to +50 mV, more preferably +10 mV to +30 mV, and most preferably +15 mV to +25 mV. Preferred dispersions of the second particle type have a zeta potential values of about −10 mV to −50 mV, more preferably −10 mV to −30 mV, and most preferably −15 mV to −25 mV. Furthermore, evaluation of the point of zero charge (isoelectric point) of metal oxides is useful to preselect metal oxides of interest, as listed in Table 1.

Surface Charge of Particulate Dispersions

The presence of charge on dispersed colloidal particles occurs by two principal mechanisms: dissociations of ionogenic surface groups or preferential absorption. Each mechanism can occur simultaneously or independently. Dissociation of acidic groups on the surface of a particle will give rise to a negatively charged surface. Conversely, dissociation of basic surface groups will result in a positively charged surface. In both cases, the magnitude of the surface charge depends on the strength of the acidic or basic groups and on the pH of the solution. The surface charge can be reduced to zero (isoelectric point) by suppressing the surface ionization. This can be achieved by decreasing the pH in the case of negatively charged particles or increased the pH in the case of positively charged particles. Furthermore, if alkali is added to a dispersion of negatively charged particles, the particles tend to become more negatively charged. If acid is added to this dispersion, then a point will be reached where the charge on the particle is neutralized. Subsequent addition of acid will cause a build up of positive charge on the particle.

Modification of Surface Charge

Adsorption of ions and ionic surfactants can be specifically adsorbed onto the charged particle surface. In the case of cationic surfactants, adsorption leads to a positively charged surface and in the case of anionic surfactants, adsorption leads to a negatively charged surface. Adsorption of single valent or multivalent inorganic ions (e.g. $Na^+$, $Al^{+3}$) can interact with charged surfaces in one of two ways: reduction of the magnitude of charge at a given pH; change in pH of the isoelectric point (point of neutral charge). The specific adsorption of ions onto a particle surface, even at low concentrations, can have a dramatic effect on the surface charge. In some cases, specific ion adsorption can lead to a charge reversal of the surface. The addition of surfactants or specific ions to particle dispersions is a common method to modify the surface charge characteristics.

TABLE 1

Point of Zero Charge (PZC) for Various Oxides in Water

| Oxide | PZC |
|---|---|
| $Ag_2O$ | 11.2 |
| $Al_2O_3$ | 9.1 |
| BeO | 10.2 |
| CdO | 11.6 |
| $CeO_2$ | 8.1 |
| CoO | 10.2 |
| $Co_3O_4$ | 7.4 |
| $Cr_2O_3$ | 7.1 |
| CuO | 9.3 |
| $Fe_2O_3$ | 8.2 |
| $Fe_3O_4$ | 6.6 |
| HgO | 7.3 |
| $La_2O_3$ | 10.1 |
| MgO | 12.4 |
| $MnO_2$ | 5.3 |
| $MoO_3$ | 2 |
| $Nb_2O_5$ | 2.8 |
| NiO | 10.2 |
| $PuO_2$ | 5.3 |
| $RuO_2$ | 9 |
| $Sb_2O_5$ | 1.9 |
| $SiO_2$ | 2 |
| SnO2 | 5.6 |
| $Ta_2O_5$ | 2.8 |
| $ThO_2$ | 9.2 |
| $TiO_2$ Rutile | 5.7 |
| $TiO_2$ Anatase | 6.2 |
| $V_2O_3$ | 8.4 |
| $WO_3$ | 0.4 |
| $Y_2O_3$ | 8.9 |
| ZnO | 9.2 |
| $ZrO_2$ | 7.6 |

Refractive Index Matching Polymers

To obtain the optical blurring effects in the cosmetic compositions of the present invention, it is necessary to incorporate a polymer whose refractive index substantially matches the refractive index of one of the fractal particles (the polymer is also referred to as the refractive index matching polymer).

Figure 2A:
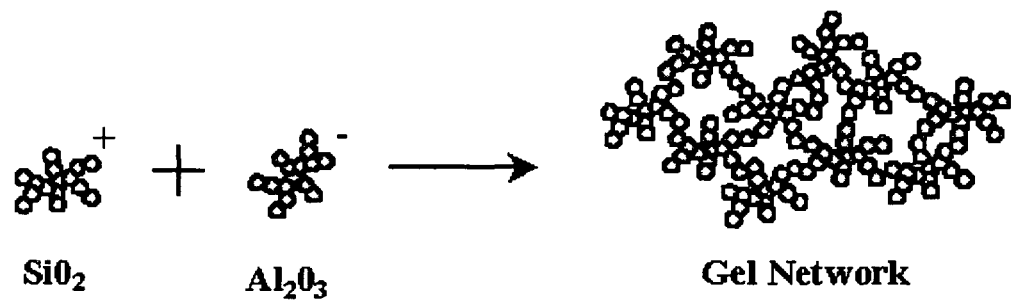
FIG. 2A depicts the formation of a gel network from aqueous dispersions of alumina and silica.

FIG. 2A depicts the formation of a gel network from aqueous dispersions $SiO_2$ and $Al_2O_3$ particles. In this depiction the $SiO_2$ particles and the $Al_2O_3$ particles are both visible when applied to a substrate in the form of a film or coating. This is shown visually in the FIG. 2A by using the same shading for all particles in the gel network.

Figure 2B:
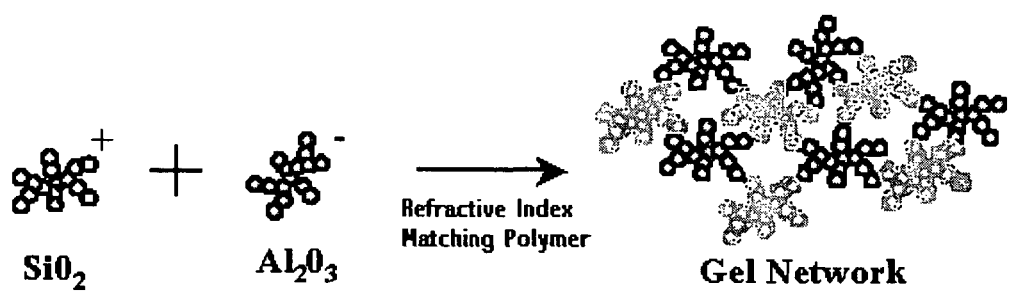
FIG. 2B depicts the formation of a gel network from aqueous dispersions of oppositely charged fractal particles and in the presence of a polymer whose refractive index substantially matches the refractive index of one of the particles.

By incorporating the refractive index matching polymer, the fractal particle whose refractive index is matched (e.g. alumina/titania, silicone/zirconia) becomes "invisible" or "optically transparent" when a film of the cosmetic composition is applied to a biologic substrate such as the skin. This is depicted in FIG. 2B in which the fractal particle whose refractive index is matched by the refractive index matching polymer is less optically apparent to the observer. This is shown visually in FIG. 2B by the light shading for the refractive index matched fractal particle in the gel network.

Figure 3:
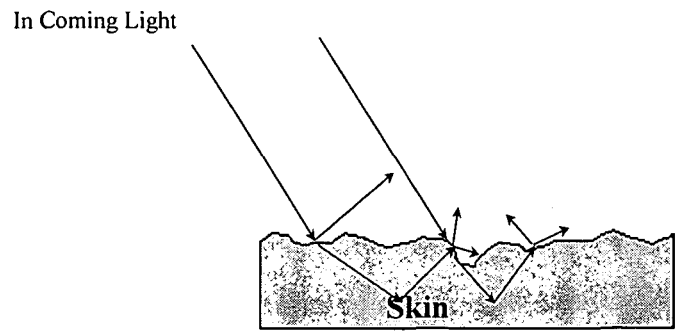
FIG. 3 depicts the rough surface created by fine lines and wrinkles that traps light, exacerbating topological features.
Figure 4:
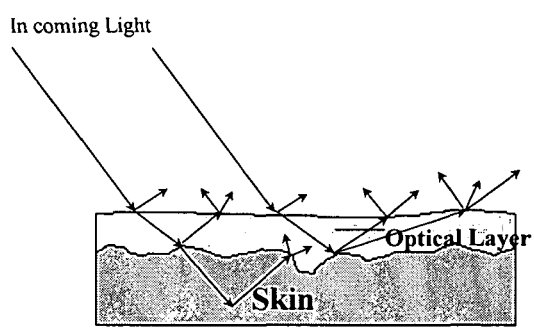
FIG. 4 depicts the optical gel layer on top of the rough skin surface.

By way of illustration, referring to FIG. 3, there is shown how the rough surface created by wrinkles and fine lines "trap" light, thereby exacerbating topological features. Referring to FIG. 4, the composition of the present invention fills in fine lines and wrinkles and diffuses reflected and transmitted light while maintaining high transparency, as indicated by the shorter vector lines for the rays of light leaving the surface.

In one embodiment the refractive index matching polymer is incorporated into the fractal gel. In this embodiment the cosmetic composition may comprise up to 100% of the fractal gel, which would include the first and second fractal particles, the solvent(s) used to disperse the fractal particles, the refractive index matching polymer, optionally one or more active components as hereinafter described, and optionally one or more adjuvants or excipients as hereinafter described. In this embodiment the fractal gel may further be present as the gel phase of a multiphase cosmetic composition, wherein the gel phase constitutes less than 100% of the cosmetic composition. The optical blurring properties of the cosmetic composition are manifest when a film of the composition is applied to the skin or other biologic substrate.

In another embodiment the cosmetic composition is a multiphase composition in which the refractive index matching polymer is present in a phase other than the fractal gel phase. Although the refractive index matching polymer is not present in the gel phase, the optical blurring benefits of the present invention are imparted to films of the cosmetic composition deposited onto biologic substrates in light of the commingling of the phases present in the composition and the shear forces that occur when the film is applied to the biologic substrate. In this embodiment the cosmetic composition comprises the fractal gel phase, which includes the first and second fractal particles, the solvent(s) used to disperse the fractal particles, optionally one or more active components as hereinafter described, and optionally one or more adjuvants or excipients as hereinafter described, and at least one additional phase, which comprises the refractive index matching polymer, solvent(s), optionally one or more active components as hereinafter described, and optionally one or more adjuvants or excipients as hereinafter described.

The gel network may be further incorporated into an oil-in-water (o/w) emulsion containing a refractive index matching polymer. Preferably, the polymer is in the fractal gel.

Suitable refractive index matching polymers may be silicone derived, organic derived including hydrocarbon derived, polar, nonpolar, hydrophilic, hydrophobic, or combinations thereof. The cosmetic composition may also contain two or more refractive index matching polymers of different types and/or molecular weights. Furthermore, the two or more refractive index matching polymers may be miscible or immiscible with one another, yet share a common refractive index, or miscible polymers may have a composite refractive index that matches the refractive index of the selected particle. The one or more refractive index matching polymers may also be distributed between the fractal gel phase and another phase in an emulsion system.

TABLE 2

Refractive Index of Selected Polymers and Solvents

| | Refractive Index | | Refractive Index |
|---|---|---|---|
| PEG-11 Methyl Ether Dimethicone[1] | 1.456 | n-Butanol | 1.399 |
| PEG-9 Dimethicone[1] | 1.420 | Butyl alcohol | 1.540 |
| PEG-9 Methyl Ether Dimethicone[1] | 1.417 | Di(ethylene glycol) | 1.446 |
| Methyl phenyl silicone fluid (F-5w 100 cs)[1] | 1.427 | Di-ethylene glycol mono ethyl ether | 1.427 |

TABLE 2-continued

Refractive Index of Selected Polymers and Solvents

| | Refractive Index | | Refractive Index |
|---|---|---|---|
| Methyl phenyl silicone fluid (KF54)[1] | 1.505 | Propylene glycol | 1.441 |
| Methicone(F-9W-9)[1] | 1.396 | Ethanol | 1.360 |
| Dimethiconol Blend 20[4] | 1.401 | Ethylene glycol | 1.431 |
| Methyl phenyl silicone(KF53)[1] | 1.485 | Ethylene glycol mono n-butyl ether | 1.419 |
| Capryl Trimethicone (Silcare 31M60)[2] | 1.410 | Glycerine | 1.474 |
| Capryl Trimethicone (Silcare 31M30)[2] | 1.440 | Glycerol | 1.472 |
| Bis(trimethylsilyl)acetate (180M10)[2] | 1.405 | n-Pentanol | 1.409 |
| Bis(trimethylsilyl)acetate (180M30)[2] | 1.478 | Dimethicone(Volasil DM 1.5)[3] | 1.382 |
| Aminopropyl Phenyltrimethicone[4] | 1.500 | Isopropyl Myristate | 1.436 |
| Hexamethydisiloxane (Volasil DM 0.65)[3] | 1.375 | Ethylhexyl methoxycinnamate | 1.545 |
| Phenyl Trimethicone[4] | 1.460 | Cetyl Ricinoleate Benzoate | 1.477 |
| Cyclomethicone (Volasil (1585)[3] | 1.395 | Propylene Glycol Dicaprylate | 1.441 |
| Poly(phenyl)methylsilsequioxane[5] | 1.540 | Caprylic/Capric triglyceride | 1.45 |

[1]Shin Etsu
[2]Clariant
[3]Chemsil
[4]Dow Corning
[5]Wacker Besil

Especially preferred for use as the RI matching polymer are silicone polymers such as Bis(trimethylsilyl)silicylate (Clariant 180M30), phenyl trimethicone (Dow Corning 556), PEG 12 Dimethicone (Dow Corning UP 1005) and mixtures thereof. This is because silica's refractive index (1.460) substantially matches that of silicones (1.400 to 1.470) used as the oil phase vehicle of oil/water emulsions. Also, especially suitable as the RI matching polymer are polyglycols, as they too have a refractive index (1.470) substantially matching the RI of silica. Suitable polyglycols are propylene glycol dicaprylate, glycerin, di(ethylene) glycol, glycerol (Solvey), and mixtures thereof. Preferably, the refractive index of the selected fractal particle should be within 0.05 of the refractive index of the refractive index matching polymeric material, more preferably, within about 0.01, and most preferably within about 0.005.

The polymers are present in the cosmetic compositions of the present invention in an amount adapted to provide a medium in which light passing through the medium is not perturbed when incident on the fractal particle whose refractive index has been matched, thereby rendering the particle transparent, i.e., "invisible" to the observer. As a guide, the amount of polymer is such that a major portion of the void volume of the fractal particle whose refractive index is matched would be occupied by the polymer The quantity of refractive index matching polymer needed to achieve a desirable effect with a selected fractal particle contained within the cosmetic composition can be estimated by determining the Oil Absorption number for the fractal particle (ATSM D 281, ASTM D 1483). Preferably the quantity of the refractive index matching polymer contained within the cosmetic composition must be at least about between 70% of the Oil Absorption number, and more preferably between 85% and 100% of the Oil Absorption number of the chosen fractal particle.

A goniospectrophotometer is a useful in-vitro tool to measure the efficacy of soft focus or blurring materials and to characterize light diffusion properties of particles and gels. One can use light intensive (L* value) at wide angles (+/−55 degrees) as a parameter to quantify soft focus effect. The method used in the following examples is similar to that of Pascal based on forward scattering by quantifying spreading (lateral diffusion) of light beam on a film as a parameter to evaluate soft focus efficacy. See "*In-vitro Method of Quantification of Soft Focus Effect of Particulates*," Pascal Delrieu, NYSCC Scientific Meeting, New York City, Dec. 8-9, 2005, incorporated by reference herein in its entirety.

The Cosmetic Compositions

The cosmetic compositions of the present invention may be formulated as single phase aqueous or nonaqueous compositions. Preferably, the cosmetic compositions according to the invention are formulated as emulsions. These emulsions may be oil-in-water (including silicone in water) emulsions, water-in-oil (including water-in-silicone) emulsions, or multiple emulsions such as oil-in-water-in-oil (o/w/o) or water-in-oil-in-water (w/o/w), but are preferably silicone-in-water emulsions. It is understood that the oil phase can comprise silicone oils, non-silicone organic oils, or mixtures thereof. While not preferred, the compositions can comprise two immiscible phases that are admixed at the time of use by shaking.

In addition to the gel phase comprising the fractal particles of the present invention and the refractive index matching polymer, the compositions of the present invention may comprise one or more active ingredients adapted to bestow a cosmetic benefit to the skin when applied to the skin as a film and/or one or more adjuvants or excipients (adjuvants and excipients are collectively referred to herein as adjuvants) to impart to the cosmetic product particular desirable physical properties, to meet product performance requirements, or to establish compositional type, e.g., emulsion (of a particular type), solution, etc. The actives and/or the adjuvants may be present in the gel phase, in another phase, or in either, as desired, or as mandated by the chemical system.

Suitable active agents include pigments to impart a color to the skin or other biologic surface; opacifiers and light diffusers; sunscreens; uv light absorbers; emollients; humectants; occlusive agents; antioxidants; exfoliants; antioxidants; anti-inflammatory agents; skin whitening agents; abrasives; anti-acne agents; hair treatment agents; humectants; emollients; moisturizers; anti-wrinkle ingredients; concealers; matte finishing agents; proteins; anti-oxidants; bronzers; solvents; ultraviolet (UV) absorbing agents; oil absorbing agents; neutralizing agents. It is understood to those skilled in the art that any other cosmetically acceptable ingredient, i.e., those included in the International Cosmetic Ingredient Dictionary and Handbook, 10th Ed. (hereinafter INCI) may be used and compatible combinations thereof.

Suitable adjuvants include film forming agents; solvents; viscosity and rheology modifiers such as thickeners; surface active agents including emulsifiers; hydrotropes; emulsion stabilizers; plasticizers; fillers and bulking agents; pH adjusting agents including buffers, acids, and bases; chelating agents; binders; propellants; fragrances; preservatives and antimicrobials, and compatible combinations thereof.

Suitable active agents and adjuvants used in cosmetic compositions of the present invention are tabulated in The International Cosmetic Ingredient Dictionary and Handbook (commonly INCI), (10th Edition, 2006) (Cosmetic and Toiletries Association). Generally, reference to specific materials utilizes the INCI adopted name nomenclature. The active agents and adjuvants are incorporated in the compositions of the present invention in amounts that provide their intended functions, as those skilled in the cosmetic arts are knowledgeable. Generally, this amount is from about 0.001 to 25%, more usually 0.01 to 15%, and especially 0.1 to 10% by weight of the composition.

The cosmetic compositions may contain polymeric light diffusers as known in the cosmetic arts, such as nylon (e.g., Nylon 12 available from Cabot as SP-500 and Orgasol 2002™), poly(methylacrylic acid) (also known as PMMA or methyl methacrylate crosspolymer; CAS No. 25777-71-3), polyethylene, polystyrene, ethylene/acrylic acid copolymer (e.g., EA-209 supplied by Kobo), and fluorinated hydrocarbons such as Teflon. The polymeric light diffusers, preferably nylon, are present in a concentration in the range of between about 0.01-10%, preferably about 0.1-5% by weight of the composition. Inorganic light diffusers can also be used, e.g., boron nitride, barium sulfate, and silicates such as calcium alumina borosilicate, and are typically present in an amount of from about 0.01 to about 10%, preferably about 0.1 to about 5% by weight.

The particle content of the cosmetic composition of the present invention ranges from about 1-80% solids, preferably about 3-40% solids, more preferably about 5-30% solids. The final dried film as applied to the skin contains about 1-80% solids, preferably about 5-60% solids, more preferably, about 10-40% solids.

The cosmetic composition of the present invention may contain a viscosity modifier such as a thickener together with emulsifiers to modify the viscosity of the composition, for example to form creams, pastes, and lotions that enhance skin feel. Suitable viscosity modifiers are starches, cellulose derivatives such as sodium carboxymethyl cellulose, methyl cellulose, ethyl cellulose, cationized cellulose, hydroxyethyl cellulose, hydroxypropyl cellulose, hydroxypropylmethyl cellulose; silicates such as veegum or clays; polysaccharides such as xanthan or guar gums, hydrophilic polymers, such as carboxyvinyl polymers, for example carbomers. Viscosity/rheology modifiers may be present in the composition in an amount of from about 0.1 to about 10% by weight of the composition.

The cosmetic emulsifier should preferably be an oil-in-water or water-in-oil emulsifier. Preferably, the oil phase is a silicone oil, and the emulsifier is a silicone emulsifier. The emulsifiers may be chosen advantageously to match the refractive index of the fractal particle whose refractive index is matched, but are not substitutes for the refractive index matching polymer.

Emulsifying agents may be present in a concentration of from about 0-10%, preferably about 0.1-6%, more preferably about 3-5%. Nonlimiting examples of suitable emulsifiers are glycerol monostearate, PEG 12 Dimethicone (Dow Corning), RM 2-2051™ (Dow Corning), an emulsion of aqueous polyacrylate emulsified into silicone (dimethicone and cyclopentasiloxane), alkylmethyl siloxanes copolyol (Dow Corning 5200), PEG 11 methylether dimethicone (Shin Etsu), cyclopentasiloxane/PEG/PPG 18/18 dimethicone (Dow Corning 5225C).

The cosmetic composition of the present invention may contain non-occlusive film-forming agents such as, but not limited to, cosmetic fluids, i.e., silicone compounds containing various combinations of elastomers in a variety of diluents. Examples of suitable cosmetic fluids are cyclopentasiloxane and amino propyldimethicone (Cosmetic fluid 1486-NH) (manufactured by Chemisil), cyclomethicone and dimethicone (Cosmetic fluid 1684-DM) (manufactured by Chemisil), and a blend of low and high viscosity polydimethylsiloxane (e.g. Dow Corning 1413 Fluid™) (Dow Corning). Preferred is a blend of high viscosity polydimethylsiloxane in low viscosity polydimethylsiloxane (e.g. Dow Corning 1413 Fluid™) (Dow Corning).

In one embodiment the cosmetic composition is nonpigmented.

In a preferred embodiment the cosmetic compositions contain one or more pigments, which are typically present in a different phase from the fractal gel phase. The pigment used herein can be inorganic and/or organic. Cosmetic compositions according to the invention comprise greater than or equal to 0.1% pigments by weight of the cosmetic composition to provide a pigmenting effect. Preferably, the pigments may be present from about 0.25% to 15%, most preferably from about 0.1 to 10% by weight The pigments are not fractal particles in accordance with the invention because they do not have the proper size domain, do not have the proper dimensionality, or are not charged particles. As used herein the term "pigments" includes lakes, and a single pigment or pigment combinations. Other colorants such as D&C dyes and self-tanning agents such as carbonyl derivatives or food colorants such as dihydroxyacetone (DHA) or erythrulose may be used. Pigments and colorants are used interchangeably herein.

Preferably, the pigments are selected from the group consisting of titanium oxides such as rutile titanium dioxide, anatase titanium dioxide, zinc oxide, zirconium oxide, iron oxides such as ferric oxide, ferrous oxide, yellow iron oxide, red iron oxide, black iron oxide, acylglutamate iron oxides, chromium oxide, chromium hydroxide, bismuth oxy chloride, manganese violet, cerium oxide, ultramarine blue, carmine, and derivatives and mixtures thereof. More preferably, the pigment is titanium oxide, yellow iron oxide, red iron oxide, black iron oxide, and mixtures thereof. The pigments can be surface modified to render them either hydrophobic or hydrophilic to interact synergistically with the fractal particle network.

The cosmetic composition may also include opacifying agents (pearlescent agents) to add optical shimmer and luster or for tactile silkiness to the touch such as, but not limited to mica, sericite (a fine grained variety of muscovite). These agents may be present in amounts from about 0.1-10%, preferably about 0.5-5%.

The cosmetic composition may also include oil phase solvents useful as base fluids for spreading and lubrication properties or as a vehicle to provide a medium for one or more of the other constituents of the cosmetic composition. These solvents include water, organic fluids, especially alcohols and hydrocarbon fluids, silicone fluids, hydrophilic and hydrophobic polymers, and the like, and may be present in a concentration of about 0.5-90%, preferably about 5-50%, most preferably 10-35%. Preferred oil phase solvents are cyclomethicones such as cyclotetrasiloxane (e.g. Cyclo-2244 Cosmetic Grade Silicone (D4) (manufactured by Clearco), cyclopentasiloxane (e.g. Cyclo-2245 Cosmetic Grade Silicone (D5) (manufactured by Clearco), a cyclopentasiloxane/cyclohexasiloxane blend (D5/D6 Blend) Cyclo-2345 Cosmetic Grade Silicone (manufactured by Clearco), and a cyclomethicone/dimethiconol blend (D5/D4 Blend) Cyclo-1400 Cosmetic Grade Silicone (manufactured by Clearco). More preferred is D5.

Water typically is present in amounts ranging from about 10% to about 90% water by weight of the composition, preferably from about 40% to about 80%, and most preferably from about 40% to about 70%. Also suitable as aqueous phase solvents are low molecular weight alcohols having less than 8 carbons, for example ethanol, propanol, hexanol, and the like, and polyhydric alcohols, especially glycols. Suitable glycols are propylene glycol, pentylene glycol, hexylene glycol, and 1,2-octanediol. Suitable polyhydric alcohols include sorbitol and glycerin. These may be present in amounts of from about 1% to about 50%, preferably 5% to 35% by weight.

Optionally, electrolytes such as sodium chloride may be added in amounts ranging from about 0-5%, preferably from about 0.5-2%.

The compositions of the invention further typically contain an amount of a pH adjusting agent to provide the desired pH of the composition and at which the fractal particles will have the requisite opposite net surface charges. Suitable pH adjusting agents are organic and mineral acids as is well known in the cosmetic arts. Buffers to maintain the established pH may also be incorporated, for example sodium lactate.

It is further understood that the other cosmetic actives and adjuvants introduced into the composition must be of a kind and quantity that are not detrimental to the advantageous effect which is sought herein according to the invention.

The composition of the present invention improves the optical properties of films of cosmetic composition, as compared to those which merely reflect light producing a shiny appearance, those which merely cover the skin and impart a white cast to the skin, or those which either result in optical blurring or space filling, but not both. The resulting composition when applied to the skin, makes the skin appear more youthful, smoother and even in tone.

Figure 5:
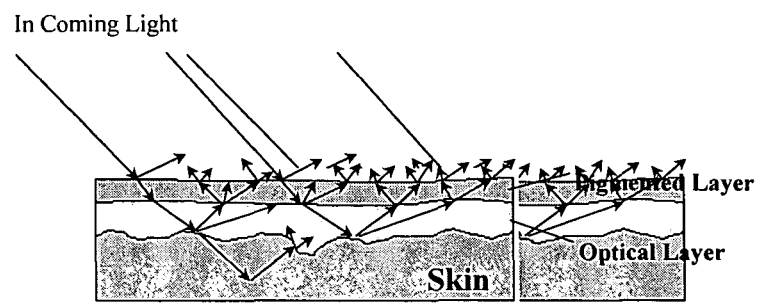
FIG. 5 depicts the optical layer when used as a primer for pigmented cosmetics.

The physical arrangement of the gel structure, high particle loading and network formation, provides a smooth surface for topcoat applications of any foundation. Referring to FIG. 5, the optical layer provides a unique "light releasing" effect from the skin when used as a primer for pigmented cosmetics. The optical layer mimics and enhances the skin's natural transparent qualities. When light penetrates the optical layer, diffuse reflection through the pigmented layer provides a "back lighting" effect, brightening foundations to give a more natural and youthful look.

The cosmetic composition may take on various forms including powder, cake, pencil, stick, ointment, cream, milk, lotion, liquid-phase, gel, emulsion, emulsified gel, mousse, foam, spray, wipes. Preferably, the cosmetic composition is used in a liquid or powder foundation.

The fractal gels may be incorporated in cosmetically acceptable vehicles, such as but not limited to, liquid (e.g. suspension or solution), gel, emulsion, emulsified gel, mousse, cream, ointment, paste, serum, milk, foam, balm, aerosol, liposomes, solid (e.g. pressed powders), anhydrous oil and wax composition. Preferably, the cosmetic composition is used in a liquid or powder foundation. More specifically, the cosmetic include facial skin care cosmetics such as skin lotion, skin milk, skin cream, gel, and make-ups such as foundation, foundation primer base, blush, lip stick, eye shadow, eye liner, nail enamel, concealer, mascara, body make-up product, or a sunscreen.

Methods of Use

The methods of use for the cosmetic compositions disclosed and claimed herein concern the improvement in the aesthetic appearance of skin and include, but are not limited to: methods of blurring or masking one or more of wrinkles, fine lines, pores, skin imperfections, especially in the facial, neck or on or around the lip areas; methods to correct imperfections in skin such as blotches, freckles, redness, spider veins, and dark rings around the eyes; methods of enhancing or modifying skin color; and methods to improve finished makeup, and methods for application to the hair, eyelashes, and eyebrows.

The compositions of the present invention are suitable for use as a hair cosmetic, in particular as a mascara, in light of the unique rheological properties exhibited by the fractal gels, as mentioned above. Thus, the compositions of the invention are free-flowing under shear, which allows them to be applied with a brush or suitable applicator. When the shear is removed the compositions return rapidly to the more viscous gel condition. Because the compositions are fractal, that is, they are porous, reticulated structures capable of maintaining geometric shape, they are able to coat hair and provide a volumizing benefit. Accordingly, they are ideal as mascaras, especially when formulated with a film former (as previously described), and as hair volumizers for treating thinning hair.

Examples of facial lines and skin imperfections which can be improved using the fractal gels of the present invention include, but are not limited to; frown lines that run between the eyebrows known as glabellar lines; perioral or smoker's lines which are vertical lines on the mouth; marionette lines at the corner of the mouth known as oral commissures; worry lines that run across the forehead; crow's feet at the corner of the eyes known as periorbital lines; deep smile lines that run from the side of the nose to corners of the mouth known as nasolabial furrows; cheek depressions; acne scars; some facial scars; wound or burn scars; keloids; to reduce dark rings around the eyes; to reduce the appearance of pores or blemishes, age spots, moles, birthmarks; to redefine the lip border; for artificial or self-tanning, and to reduce skin color unevenness or dullness.

In one embodiment the fractal gel of the present invention is a spreadable, flowable and greaseless cosmetic composition useful for, but not limited to, foundation products, finishing powders, blushers, concealers, skin care products, mascara, lip products, and the like. It can be incorporated in a skin care or make-up formulation in a quantity sufficient for efficient blurring. In another embodiment, the solid compositions are substantially gelled to have a solid-like self-supporting body.

A person skilled in the art can select the appropriate presentation form, and also the method of preparing it, on the basis of general knowledge, taking into account the nature of the constituents used and the intended use of the composition.

Facial lines and wrinkles can be present anywhere on the face, and occur most frequently on the lips and in the eye area. However, it is understood by those skilled in the art that the composition can be applied to any part of the body where a blurring effect is desired such as to reduce wrinkles, fine lines, pores, and skin imperfections. Non-limiting examples include to conceal imperfections in the skin, such as to mask the appearance of cellulite or vitiligo, to mask the appearance of spider vessels, moles, age spots, blemishes, acne marks and scars, freckles, birth marks and varicose veins, to conceal damage incurred to the skin as a result of trauma such as cosmetic surgery, burns, stretching of skin, to conceal the appearance of villus hair on the skin; to provide UV protection to the skin.

The compositions herein can be used by topically applying to the areas of the skin a safe and effective amount of the compositions. The effective amount can easily be determined by each user.

As used herein the term, "safe and effective amount" refers to a sufficient amount of a compound, composition or other material described by this phrase to significantly induce a both "optical blurring" and space filling of the appearance of the skin, but low enough to avoid undue side effects (e.g., significant skin irritation or sensitization), within the scope of sound judgment of the skilled person. The safe and effective amount of the compound, composition or other material may vary with the particular skin being treated, the age and physical condition of the biological subject being treated, the severity of the skin condition, the duration of treatment, the nature of concurrent therapy, the specific compound, composition, or other material employed, the particular cosmetically acceptable topical carrier utilized, and the factors within the knowledge and expertise of the skilled person.

The composition can be applied once, twice or more times for several days, weeks, months or years, at any intervals. The compositions may be applied in accordance with a particular regimen, for example, everyday for one, two, or more weeks, or may be intended for continued daily use.

The make-up compositions of the present invention may also be intended for removal following a period of use, with reapplication when desired. The compositions are generally applied by light massaging the composition onto the skin. However, the method of application may be any method known in the art and is thus not limited to the aforementioned. Where necessary the compositions can be removed using soap and water or other cosmetic cleansers.

The invention also relates to a method for therapeutic treatment of the skin. It is further understood that the fractal gel of the present invention may be used together with therapeutic agents, together with or adjunctive to pharmaceutical compositions including, but not limited to, anti-acne agents, self-tanning ingredients, anti-inflammatory agents, anti-bacterials, anti-fungals, anti-virals, anti-yeast agents, eye treatments, analgesics, antidandruff and antiseborrhetic agents, hyperkeratolytics, antipsoriatic agents, skin lightening agents, agents, wound healing agents, burn treatments, tanning agents, hair treatment agents, hair growth products, wart removers, antipuretics, and hormones.

The fractal gel of the present invention may be used together with cosmetic agents including, but not limited to emollients, sunscreens, age spot treatments, depigmenting agents, anti-aging agents such as exfoliants, anti-glycation endpoint blockers, and the like. In particular sunscreens and uv filters are an important cosmetic active in skin care products generally to prevent the harmful rays of the sun from exacerbating the aging process. These actives are typically present in an amount to provide an SPF value of from 2 to about 50, preferably from about 6 to about 30.

A person skilled in the art can select the appropriate presentation form, and also the method of preparing it, on the basis of general knowledge, taking into account the nature of the constituents used and the intended use of the composition.

Kits containing the above compositions are also contemplated. Compositions of the present invention can be packaged to contain, separately or in kit form together with a container, instructions or instruction brochure.

Preparation

The compositions useful for the methods of the present invention are generally prepared by conventional methods such as are known in the art of making topical compositions. Such methods typically involve mixing of the ingredients in one or more steps to a relatively uniform state, with or without heating, cooling, application of vacuum, and the like. Typically, the fractal gel is made by preparing a dispersion of each fractal particle in a suitable solvent (dispersant), adjusting the dispersion pH with a pH adjusting agent, and admixing the dispersions with shear to permit the formation of the gel. In some instances owing to the properties of the constituents it may be necessary to preheat one or both of the dispersants. The pH adjusting agent may also be provided into the admixed dispersions rather than into each dispersion individually. The refractive index matching polymer may then be incorporated into the gel, along with any actives and adjuvants that are desired. Certain of the adjuvants may require addition as premixes with a solvent, as generally known in the cosmetic art. The resulting gel can be employed as it is and can itself constitute a skin care or make-up composition for blurring wrinkles and skin imperfections.

Alternatively, the fractal gel may be incorporated into a multiphase cosmetic composition as previously mentioned. The other phase may be prepared in accordance with known methods, for example forming one or more premixes of the ingredients for combination with the fractal gel. As previously mentioned the polymer in whole or in part may be incorporated into this other phase. Where premixes have been formed at elevated temperatures appropriate cooling of the composition to establish the emulsion will be necessary.

The following examples describe specific aspects of the invention to illustrate the invention and provide a description of the present methods for those skilled in the art. The Examples should not be construed as limiting the invention as the examples merely provide specific methodology useful in the understanding and practice of the invention and its various aspects.

While certain preferred and alternative embodiments of the invention have been set forth for purposes of disclosing the invention, modification to the disclosed embodiments can occur to those who are skilled in the art.

EXAMPLES

Example 1

Fractal Gel

The following example illustrates the use of combining high and low surface area particulates to form a fractal gel network and is not intended to be limiting.

TABLE 3

| Dispersion 1 | |
|---|---|
| Silica | 30% |
| Water | 68.6% |
| Glycolic Acid | 1.4% |
| Dispersion 2 | |
| Alumina | 60% |
| Water | 38.6% |
| Glycolic Acid | 1.4% |

Silica supplied by Degussa R380.
Alumina supplied by Cabot Spectral Al 51 or Spectral Al 80.

The particle dispersion is made using a high shear mixer equipped with a cooling jacket. The water (75% of the total) and glycolic acid were added to the mixer. Under high shear, the silica was added slowly. Once the silica was added, the dispersion was allowed to mix for 5 minutes under high shear. Lastly, the remaining 25% of water was added, and allowed to mix for an additional 5 minutes under high shear. Acidity of the dispersion was adjusted to pH 4 using basic salts solutions such as sodium hydroxide or ammonium hydroxide. Each particle dispersion was made in a similar manner. Furthermore, predetermined quantities of each particle dispersion were blended using a high-speed mixer to achieve the desired silica and alumina content of the gel. Once mixed, the resulting gel was subsequently blended with a suitable cosmetic carrier.

Example 2

Evaluation of Optical Blurring Capability of the Fractal Gels

Using a Model GSP-1B goniospectrophotometer (Murakami Color Research Laboratory), the experiments were run in transmittance mode. The angle of the light source was varied from −65° to +65°. Data was collected at every 10° increments. The light intensity (represented by L* value) in transmission mode changed with angle. The light intensity decreased from low to high angles as the source moved away from the normal. Thus, a bell shaped curve was obtained for these translucent samples.

The light diffusion profile of skin (translucent) is believed to be similar to the shape of a bell curve wherein a natural look is defined by diminished L* values at low incident angles of transmittance indicating increased subsurface light diffusion and augmented L* values at high incident angles of transmittance indicative of optical blurring effects. Preferred compositions are those wherein the difference between L* values obtained at low angles of transmission and L* values obtained at high angles of transmission are minimized. Furthermore, it is desirable to have lower L* values at small angles of incident transmission.

Samples evaluated in this study were: 1) The cosmetic composition of Table 4 with no particles (Control); 2) The Control composition of Table 4 with 10 wt % fractal particle gel network (2/1: silica/alumina) (Invention); and 3) The Control composition of Table 4 with 10 wt % spherical nylon having an average diameter of 12.5 microns and a surface area of 4 m²/g (available from Lipo Chemicals) (Reference).

TABLE 4

Cosmetic Composition

| | Description | wt % |
|---|---|---|
| 1 | Demineralized Water | 33.3 |
| 2 | Glycerin | 5.4 |
| 3 | Butylene glycol | 3.2 |
| 4 | PPG-1 Isoceteth-3 acetate | 8.6 |
| 5 | Octyldodecyl neopenanoate | 4.3 |
| 6 | glyceral stearate/PEG-75 stearate | 4.9 |
| 7 | steareth-2 | 1.6 |
| 8 | glyceral monostearate-NS emulsifier | 2.7 |
| 9 | isocetyl stearate | 6.9 |
| 10 | c12–c15 alcohol benzoate | 6.0 |
| 11 | cyclomethicone pentamer | 10.8 |
| 12 | dimethicone 50 ct | 5.4 |
| 13 | dimethiconol | 1.1 |
| 14 | dimethicon-polysilicone-1/PET | 1.3 |
| 15 | Dimethyl polysiloxane | 4.3 |
| | total | 100.0 |

Samples were cast on clean, colorless glass plates and dried overnight (2 mil wet films≈75 μm). The final thicknesses of these dried films cannot be determined, as the solid content of the different formulations were not known. Replicate samples were not run.

Figure 6:
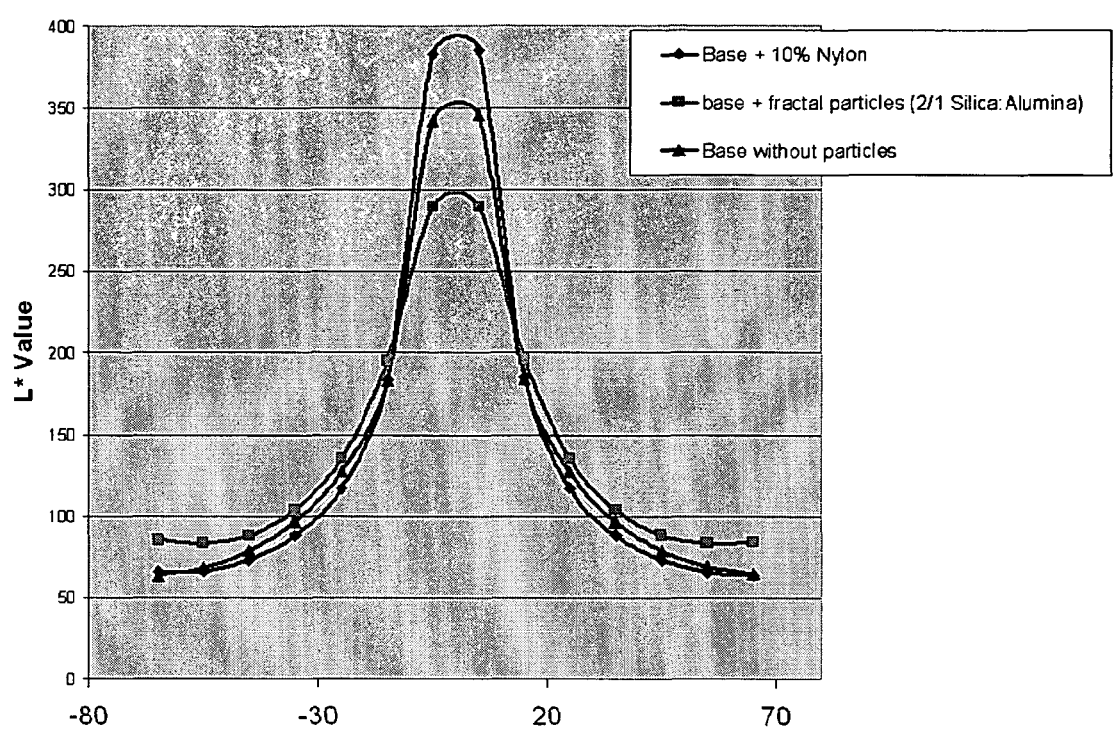
FIG. 6 depicts the angular dependence of transmitted light, reported as L* value, through a thin film of a cosmetic composition, a thin film of a cosmetic composition containing a fractal gel network, and thin film of a cosmetic composition containing spherical nylon particles.

FIG. 6 shows the angular dependence of L* value of transmitted light measured from −65 to +65 degrees with respect to the normal surface, of 1) gel base with no particles; 2) cosmetic composition 10 wt % with fractal particles gel network, and 3) cosmetic composition with 10 wt % nylon. To optimize the improve when applied to skin or other biologic surface, the difference between the peak L* value and the high (or low angle) L* value is to be minimized, thereby mimicking natural, translucent quality of the skin. The film containing the fractal particles shows a broadening of the bell curve indicative of the sought after optical properties for a cosmetic composition, as compared to the cosmetic base composition and that composition containing nylon particles. As seen in FIG. 6, the addition of nylon particles to the Control does not have an impact on the transmission profile of the Control and the film of the nylon-containing composition is more transparent at low angles compared to the Control.

Figure 7:
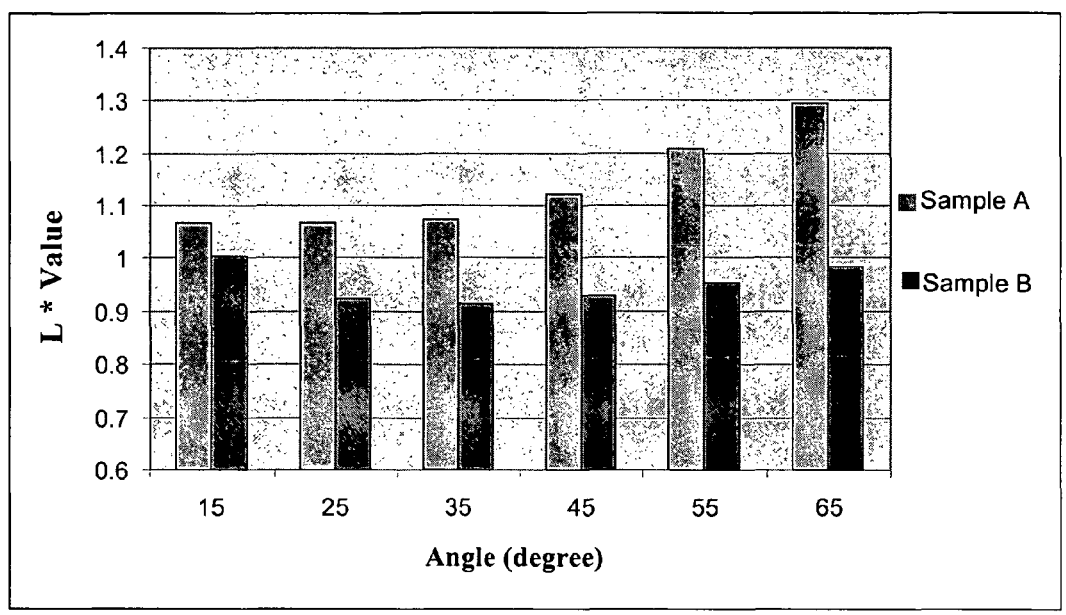
FIG. 7 depicts improved optical characteristics of a cosmetic composition containing the fractal particle gels versus traditional blurring particulates at equal solids content, the data being normalized with respect to the optical characteristics of the cosmetic composition.

FIG. 7 shows the average L* values of the cosmetic composition containing 10 wt % fractal particle gel network (Sample A) and of the cosmetic composition containing 10 wt % nylon (Sample B), normalized with respect to the L* values of the cosmetic composition containing no particles. The L* values range from 15 to 65 degrees with respect to the normal surface. Larger relative L* values denote improved optical blurring properties of the composition. The plot further illustrates the effectiveness of the of the fractal particle gel network to impart beneficial optical blurring effects over traditional particulate materials (low L* values at small transmittance angles, and higher L* values at large transmittance angles).

The results show that the gels of the present invention have superior optical properties to yield highly efficacious soft focus effects in cosmetics. Specifically, fractal particles have a unique architecture lending them to better as blurring compared to nylon.

Example 3

Table 5 below provides examples of cosmetic compositions of the fractal particle gels incorporated into an oil-in-water emulsion.

TABLE 5

Typical non-pigmented and pigmented cosmetic compositions

| | | I | II | III | VI | V | VI | VII |
|---|---|---|---|---|---|---|---|---|
| 1 | Alumina[1] | 12.0 | 13.3 | 7.5 | 27.0 | 24.0 | 21.0 | 12.0 |
| 2 | Silica[2] | 3.0 | 6.7 | 7.5 | 1.5 | 3.0 | 4.5 | 3.0 |
| 3 | Demineralized Water | 51.7 | 51.7 | 51.7 | 38.2 | 39.5 | 41.3 | 45.2 |
| 4 | Glycerin | 2.7 | 1.1 | 2.7 | 2.7 | 2.7 | 2.7 | 2.7 |
| 5 | Butylene glycol | 1.6 | 0.7 | 1.6 | 1.6 | 1.6 | 1.6 | 1.6 |

TABLE 5-continued

Typical non-pigmented and pigmented cosmetic compositions

|  | I | II | III | VI | V | VI | VII |
|---|---|---|---|---|---|---|---|
| 6 PPG-1 Isoceteth-3 acetate | 4.3 | 3.6 | 4.3 | 4.3 | 4.3 | 4.3 | 4.3 |
| 7 Octyldodecyl neopenanoate | 2.2 | 1.8 | 2.2 | 2.2 | 2.1 | 2.2 | 2.2 |
| 8 Glyceral stearate/PEG-75 stearate | 2.4 | 2.1 | 2.4 | 2.4 | 2.4 | 2.4 | 2.4 |
| 9 Steareth-2 | 0.8 | 0.7 | 0.8 | 0.8 | 0.8 | 0.8 | 0.8 |
| 10 Glyceral monostearate-NS emulsifier | 1.3 | 1.1 | 1.3 | 1.4 | 1.3 | 1.4 | 1.3 |
| 11 Isocetyl stearate | 3.5 | 2.9 | 3.5 | 3.5 | 3.4 | 3.5 | 3.5 |
| 12 C12–C15 alcohol benzoate | 3.0 | 2.6 | 3.0 | 3.0 | 3.0 | 3.0 | 3.0 |
| 13 Cyclomethicone pentamer | 5.4 | 4.6 | 5.4 | 5.4 | 5.4 | 5.4 | 4.4 |
| 14 Dimethicone 50 ct | 2.7 | 2.3 | 2.7 | 2.2 | 2.1 | 2.2 | 2.7 |
| 15 Dimethiconol | 0.5 | 0.5 | 0.5 | 0.5 | 0.5 | 0.5 | 0.5 |
| 16 Dimethicon-polysilicone-1/PET | 0.7 | 0.6 | 0.7 | 0.7 | 0.7 | 0.7 | 0.7 |
| 17 Dimethyl polysiloxane | 2.2 | 1.8 | 2.2 | 1.9 | 1.9 | 0.3 | 1.2 |
| 18 silcone elastomer[3] |  |  |  | 0.8 | 1.1 | 2.2 |  |
| 19 Phenyl trimethicone |  | 2.0 |  |  |  |  | 3.5 |
| 20 Chromalite Pigments[4] |  |  |  |  |  |  | 5.0 |
| Total | 100.0 | 100.0 | 100.0 | 100.0 | 100.0 | 100.0 | 100.0 |

[1] Cabot Spectral Al 51
[2] Deguss R380
[3] Gransil PM
[4] Engelhard
Silica index matched (1.470) by
Glycerin (1.474)
Butylene Glycol (1.439)
Octyldodecyl neopetanote (1.430)
Isocetyol stearate (1.446)
Phenyl trimethicone (1.4549 to 1.4626)
Silicone Elastomer (1.498)

The formulations of Examples I to VII for Table 5 are prepared as follows: the constituents are mixed together in accordance with the procedures set forth below.

Oil-in-water emulsions are formed in the following manner. Aqueous components are placed in a 1 liter beaker and subsequently heated to 120° F. using a hot plate. A homogenizer (Silverson L4RT) equipped with a high speed homogenization head (¾ tubular type impeller using an emulsifier screen) is used to mix the aqueous composition at 3600 rpm. The components of the oil phase are added in a separate 1 liter beaker and thoroughly mixed prior to adding to the aqueous composition. The oil phase is added slowly under high shear mixing (greater than 5000 rpm) and allowed to mix for 30 minutes once at 120° F. The emulsion is allowed to cool to room temperature under low shear, 300 rpm. Once cool, the emulsion composition is mixed under low shear, 200-400 rpm with the fractal particle gel in pre-determined quantities. The resulting make-up composition is then ready for packaging.

The invention claimed is:

1. A cosmetic composition for application to a biologic substrate wherein said composition comprises:
   a) a fractal gel network comprising a first fractal particle having a zeta potential value in a range from about +10 mV to +50 mV and a second fractal particle having a zeta potential value in a range from about −10 mV to −50 mV wherein the first fractal particle and second fractal particle are of opposite surface charges at a given pH wherein the fractal gel is formed from the association of the first fractal particle and the second fractal particle, each fractal particle having a refractive index; and
   b) a polymer that has a refractive index that substantially matches the refractive index of one of the fractal particles.

2. The cosmetic composition of claim 1, wherein the cosmetic composition is an emulsion.

3. The cosmetic composition of claim 2, wherein the emulsion is an oil-in-water emulsion.

4. The cosmetic composition of claim 3, wherein the emulsion is a silicone-in-water emulsion.

5. The cosmetic composition as in claim 1, wherein said fractal particles have a diameter of about 50-300 nm.

6. The cosmetic composition as in claim 5, wherein said fractal particles have a diameter of about 100-250 nm.

7. The cosmetic composition as in claim 1, wherein said fractal particles are metal oxide particles selected from the group consisting of fumed silica, fumed alumina, fumed titania, fumed zirconia, fumed ceria, fumed zinc oxide, fumed indium tin oxide, and mixtures thereof.

8. The cosmetic composition as in claim 1, wherein said fractal particles comprise from about 5% to about 80% by weight of the composition.

9. The cosmetic composition as in claim 1 wherein the refractive index matching polymer is selected from the group consisting of silicone derived, organic derived, polar, nonpolar, hydrophilic, hydrophobic, and combinations thereof.

10. The cosmetic composition as in claim 9 wherein the refractive index matching polymer is a polyglycol.

11. The cosmetic composition as in claim 9 wherein the refractive index matching polymer is selected from the group consisting of Bis(trimethylsilyl)silicylate, phenyl trimethicone, PEG 12 Dimethicone, propylene glycol dicaprylate, glycerin, di(ethylene) glycol, glycerol, and mixtures thereof.

12. The cosmetic composition as in claim 1 wherein the refractive index matching polymer is present in an amount of about 70% and above of the oil absorption number for the refractive index matched fractal particle.

13. The cosmetic composition of claim 1 wherein the refractive index of the refractive index matching polymer is within about 0.05 or less of the refractive index of the fractal particle.

14. The cosmetic composition as in claim 13 wherein the refractive index matching polymer is within about 0.005 or less of the refractive index of the fractal particle.

15. The cosmetic composition of claim 1 further comprising a solvent.

16. The cosmetic composition of claim 15 wherein the solvent is selected from the group consisting of water, organic fluids, silicone fluids, hydrophilic and hydrophobic polymers.

17. The cosmetic composition of claim 1 further comprising polymeric light diffusing agents selected from the group consisting of nylon, poly(methyl acrylic acid), boron nitride, barium sulfate, polyethylene, polystyrene, ethylene/acrylic acid copolymer, fluorinated hydrocarbons, silicates and silicone, and mixtures and derivatives thereof.

18. The cosmetic composition of claim 1, further comprising a particle content of about 1% to about 80% solids by weight of the composition.

19. The cosmetic composition of claim 18, further comprising a particle content of about 10% to about 40% solids by weight of the composition.

20. The cosmetic composition of claim 1, further comprising a film forming agent.

21. The cosmetic composition of claim 20, wherein said film forming agent is selected from the group consisting of amino propyldimethicone, dimethicone, and a blend of low and high viscosity polydimethylsiloxane.

22. The cosmetic composition of claim 1 further comprising pigments.

23. The cosmetic composition of claim 1 further comprising an emulsifying agent.

24. The cosmetic composition of claim 23 wherein said emulsifying agent comprises an oil-in-water emulsifier.

25. The cosmetic composition of claim 24 wherein said oil-in-water emulsifier comprises a silicone emulsifier.

26. The cosmetic composition of claim 1 further comprising one or more ingredients selected from the group consisting of electrolytes, water, humectants, emollients, moisturizers, anti-wrinkle ingredients, concealers, matte finishing agents, pigments, proteins, anti-oxidants, chelating agents, solvents, emulsifiers, sunscreens, ultraviolet absorbing agents, oil absorbing agents, fragrances, preservatives, and pH adjusting agents present in an amount to provide their intended function.

27. A foundation composition comprising:
   a) a fractal gel network of two or more types of fractal particles having opposite surface charge at a given pH, wherein the fractal gel network is formed from the association of the two or more types of fractal particles, wherein at least a first fractal particle has a zeta potential value in a range of about +10 mV to +50 mV and at least a second fractal particle has a zeta potential value in a range of about −10 mV to −50 mV;
   b) macroscopic elastomeric particles;
   c) a pigment; and
   d) a film forming agent;
   wherein said fractal gel network is further incorporated into an emulsion containing a refractive index matching polymer to at least one of the fractal particles.

28. A primer composition comprising:
   a) a fractal gel network of two or more types of fractal particles having opposite surface charge at a given pH, wherein the fractal gel network is formed from the association of the two or more types of fractal particles, wherein at least a first fractal particle has a zeta potential value in a range of about +10 mV to +50 mV and at least a second fractal particle has a zeta potential value in a range of about −10 mV to -50 mV;
   b) macroscopic elastomeric particles; and
   c) a film forming agent;
   wherein said gel network is further incorporated into an emulsion containing a refractive index matching polymer to at least one of the fractal particles.

29. A cosmetic composition according to claim 27, wherein such composition is in the form selected from the group consisting of powder, cake, pencil, stick, ointment, cream, milk, lotion, liquid-phase, gel, emulsion, emulsified gel, mousse, foam, spray, wipes, liquid paste, serum, milk, balm, aerosol, liposomes, solid, anhydrous oil and wax composition.

30. A cosmetic composition according to claim 28, wherein such composition is in the form selected from the group consisting of powder, cake, pencil, stick, ointment, cream, milk, lotion, liquid-phase, gel, emulsion, emulsified gel, mousse, foam, spray, wipes, liquid, paste, serum, milk, balm, aerosol, liposomes, solid, anhydrous oil and wax composition.

31. A cosmetic composition according to claim 1, such that the composition is a skin care cosmetic selected from the group consisting of a skin lotion, skin milk, skin cream, gel, foundation, foundation primer base, blush, lip stick, eye shadow, eye liner, nail enamel, concealer, mascara, body make-up product, and sunscreen.

32. A cosmetic composition according to claim 1, wherein the composition is a make-up composition and/or a care composition for the skin and lips.

33. A method of improving the aesthetic appearance of skin by reducing and/or masking one or more of wrinkles, fine lines, pores, skin imperfections, and skin topology wherein said method comprises the step of applying to the areas of skin to be treated an effective amount of the composition of claim 1.

34. A method of improving the aesthetic appearance of skin by reducing and/or masking one or more of wrinkles, fine lines, pores, skin imperfections, and skin topology wherein said method comprises:
   a) applying to the areas of skin to be treated an effective amount of the composition of claim 1; and
   b) applying any foundation over (a).

35. A cosmetic kit comprising:
   a) a cosmetic composition as in claim 1;
   b) instructions on how to use said cosmetic composition; and
   c) a container for holding both a) and b).

36. The method of claim 34 wherein the composition further comprises a pigment.

* * * * *